US008415514B2

(12) United States Patent  (10) Patent No.: US 8,415,514 B2
Trauth  (45) Date of Patent: Apr. 9, 2013

(54) ISOTHERMAL REACTOR FOR HYDROCARBON NITRATION

(75) Inventor: Daniel M. Trauth, Crystal Lake, IL (US)

(73) Assignee: ANGUS Chemical Company, Buffalo Grove, IL (US)

(*) Notice: Subject to any disclaimer, the term of this patent is extended or adjusted under 35 U.S.C. 154(b) by 257 days.

(21) Appl. No.: 12/879,799

(22) Filed: Sep. 10, 2010

(65) Prior Publication Data

US 2011/0092737 A1   Apr. 21, 2011

Related U.S. Application Data

(60) Provisional application No. 61/253,147, filed on Oct. 20, 2009.

(51) Int. Cl.
*C07C 201/06* (2006.01)
*C07C 201/08* (2006.01)

(52) U.S. Cl. .......................................... 568/947

(58) Field of Classification Search ............... 568/947, 568/948
See application file for complete search history.

(56) References Cited

U.S. PATENT DOCUMENTS

| | | | |
|---|---|---|---|
| 1,967,667 A | 7/1934 | Hass et al. | |
| 2,343,534 A | 3/1944 | Cavanaugh et al. | |
| 2,418,241 A * | 4/1947 | Stengel et al. | 568/947 |
| 2,455,425 A | 12/1948 | Levy et al. | |
| 2,465,959 A | 3/1949 | Tindall | |
| 2,489,320 A | 11/1949 | Nygaard et al. | |
| 2,491,919 A | 12/1949 | Egly | |
| 2,511,454 A | 6/1950 | Bishop et al. | |
| 2,512,587 A * | 6/1950 | Stengel | 568/947 |
| 2,575,855 A | 11/1951 | Stengel et al. | |
| 2,654,658 A | 10/1953 | Marshall | |
| 2,654,788 A * | 10/1953 | Marshall, Jr. | 568/939 |
| 2,789,136 A | 4/1957 | O'Hara | |
| 2,844,634 A | 7/1958 | McKinnis | |
| 3,035,100 A | 5/1962 | Kirby et al. | |
| 3,133,124 A * | 5/1964 | Bonfield | 568/942 |
| 3,173,961 A | 3/1965 | Drimus et al. | |
| 3,657,364 A | 4/1972 | Crawford et al. | |
| 3,869,253 A | 3/1975 | L'honore et al. | |
| 3,917,705 A * | 11/1975 | Swanson et al. | 564/494 |
| 4,313,009 A | 1/1982 | L'honore et al. | |
| 4,329,523 A * | 5/1982 | James et al. | 568/948 |
| 4,394,220 A | 7/1983 | Egly et al. | |
| 4,458,094 A | 7/1984 | Sherwin | |
| 4,476,336 A | 10/1984 | Sherwin | |
| 4,518,811 A | 5/1985 | Lhonroé et al. | |
| 4,626,607 A | 12/1986 | Jacquinot et al. | |
| 2011/0028731 A1 | 2/2011 | Trauth et al. | |
| 2011/0028732 A1 | 2/2011 | Trauth et al. | |
| 2011/0092748 A1 | 4/2011 | Sawant et al. | |
| 2011/0092749 A1 | 4/2011 | Sawant et al. | |
| 2011/0092750 A1 | 4/2011 | Trauth et al. | |
| 2011/0160496 A1 | 6/2011 | Sawant et al. | |

FOREIGN PATENT DOCUMENTS

| | | |
|---|---|---|
| EP | 0151074 A2 | 8/1985 |
| EP | 0171052 A2 | 2/1986 |
| GB | 916954 | 1/1963 |
| WO | WO2009129099 | 10/2009 |
| WO | WO2011049681 | 4/2011 |
| WO | WO2011049682 | 4/2011 |
| WO | WO2011049683 | 4/2011 |
| WO | WO2011078931 | 6/2011 |

OTHER PUBLICATIONS

Albright, Lyle F., Nitration of Paraffins, Chemical Engineering, Jun. 6, 1966, pp. 149-156.
PCT Written Opinion of the International Preliminary Examining Authority, PCT International Application No. PCT/US2010/048482, mailed Oct. 18, 2011.
PCT International Preliminary Report on Patentability, PCT International Application No. PCT/US2010/048482, mailed Jan. 24, 2012.
PCT International Search Report and PCT Written Opinion, PCT International Application No. PCT/US2010/048482, mailed Nov. 17, 2010.
Olujic Z. et al., "Equipment improvement trend in distillation", Chemical Engineering and Processing, vol. 48, Mar. 26, 2009, pp. 1089-1104.
PCT Written Opinion of the International Preliminary Examining Authority, PCT International Application No. PCT/US2010/048487, mailed Oct. 18, 2011.
PCT International Preliminary Report on Patentability, PCT International Application No. PCT/US2010/048487, mailed Feb. 20, 2012.
PCT Written Opinion of the International Preliminary Examining Authority, PCT International Application No. PCT/US2010/057628, mailed Feb. 14, 2012.
PCT International Preliminary Report on Patentability, PCT International Application No. PCT/US201048480, mailed May 3, 2012.
PCT International Search Report and Written Opinion, PCT International Application No. PCT/US2010048480, mailed Mar. 2, 2011.
PCT International Preliminary Report on Patentability, PCT International Application No. PCT/US2010/057628, mailed Jul. 6, 2012.
PCT Written Opinion of the International Preliminary Examining Authority, PCT International Application No. PCT/US2010/057628, mailed Apr. 4, 2012.
PCT International Search Report and Written Opinion, PCT International Application No. PCT/US2010/057628, mailed Mar. 31, 2011.
Reply to Written Opinion, PCT International Application No. PCT/US2010/048482, filed Aug. 16, 2011.
Reply to Written Opinion, PCT International Application No. PCT/US2010/048487, filed Aug. 16, 2011.
Reply to Written Opinion, PCT International Application No. PCT/US2010/057628, filed Oct. 19, 2011.
Office Action, U.S. Appl. No. 12/879,824, mailed Sep. 21, 2012.
PCT International Search Report and Written Opinion, PCT International Application No. PCT/US2010/048487, mailed Feb. 28, 2011.

* cited by examiner

*Primary Examiner* — Brian J Davis
(74) *Attorney, Agent, or Firm* — McDonnell Boehnen Hulbert & Berghoff LLP

(57) ABSTRACT

Disclosed are a process and an apparatus for synthesizing nitroalkanes by reaction of a hydrocarbon feedstock with aqueous nitric acid. By using an isothermal reactor with multiple input ports for aqueous nitric acid, a hydrocarbon feedstock may be sequentially exposed to a plurality of flows of aqueous nitric acid as it flows through the reactor.

15 Claims, 1 Drawing Sheet

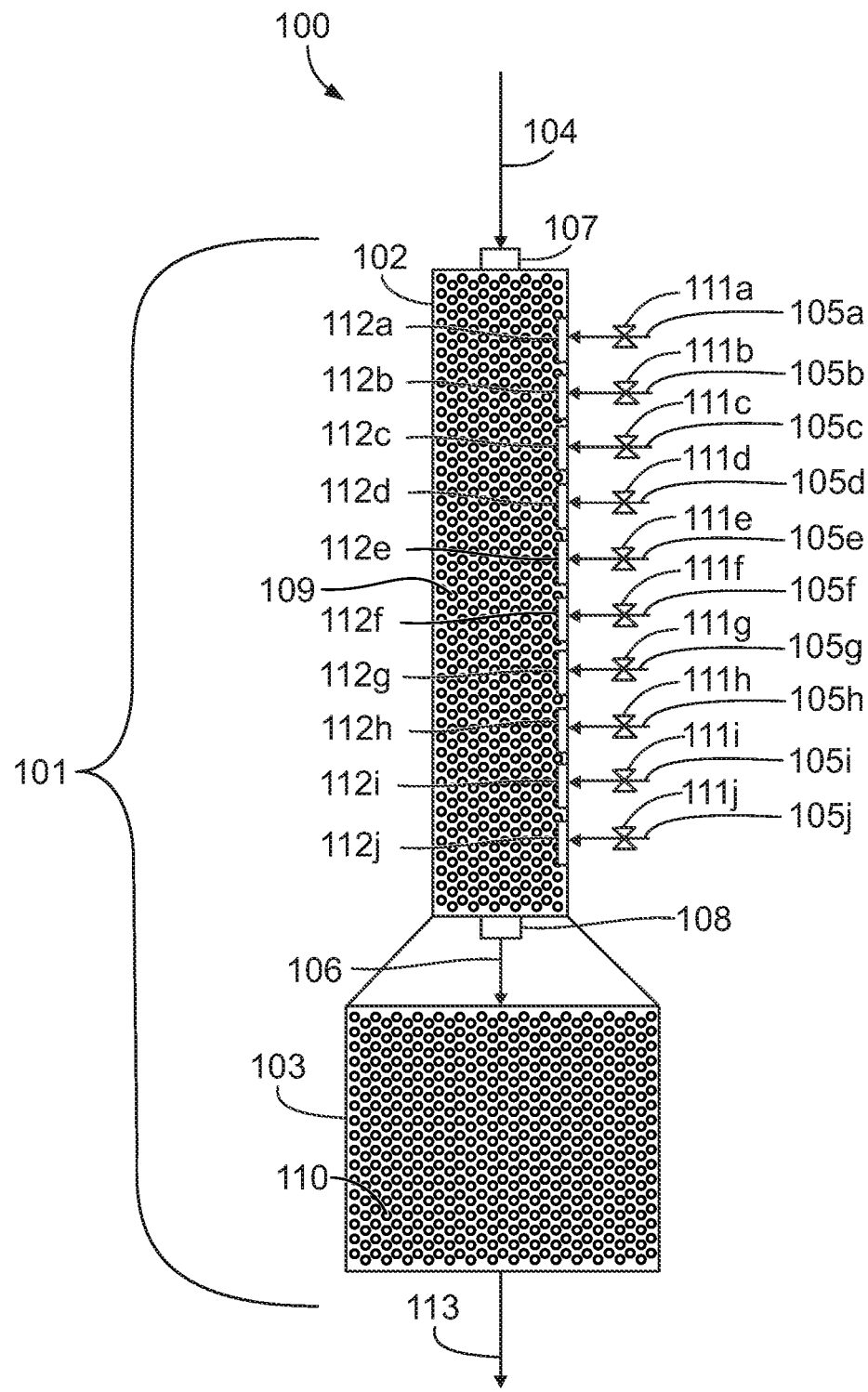

ers a reactor design that reduces potential corrosion issues.

ISOTHERMAL REACTOR FOR HYDROCARBON NITRATION

CROSS-REFERENCE TO RELATED APPLICATIONS

This application claims priority to U.S. Provisional Application No. 61/253,147, filed Oct. 20, 2009, which is hereby incorporated herein by reference in its entirety.

FIELD

This invention relates to a process for synthesizing nitroalkanes. More specifically, this invention relates to an isothermal reactor with multiple input ports for introducing aqueous nitric acid such that a hydrocarbon feedstock is sequentially exposed to a plurality of flows of aqueous nitric acid as it flows through the reactor.

BACKGROUND

The nitration of hydrocarbons generally produces a variety of products depending upon the reaction conditions and the feedstock structure. For instance, the commercial vapor phase process for propane nitration results in a mixture of four nitroparaffin products (nitromethane, 1-nitropropane, 2-nitropropane, and nitroethane) in essentially fixed relative concentrations.

Certain products, however, may be more desirable than others, and it has been a long-time goal to selectively produce the more useful nitrated compounds at the expense of the less useful compounds. Conventional reactor designs have potential mixing, temperature control, and corrosion issues. In addition, because conventional reactors do not exhibit high selectivity towards the desired products, the downstream separation process can be very capital intensive. A need exists, therefore, for more economical and selective processes and reactors for the manufacture of selectively nitrated nitroparaffins.

BRIEF SUMMARY

In one aspect, a process for synthesizing at least one nitroalkane is provided. The process comprises: reacting a hydrocarbon feedstock with aqueous nitric acid in a reactor to produce a reaction product, wherein the hydrocarbon feedstock is sequentially exposed to a plurality of flows of aqueous nitric acid as the hydrocarbon feedstock flows through at least a portion of the reactor; and recovering the at least one nitroalkane from the reaction product.

In another aspect, another process for synthesizing at least one nitroalkane is provided. The process comprises: sequentially reacting a hydrocarbon feedstock with aqueous nitric acid in a first reactor section to provide a first output stream, wherein the aqueous nitric acid is introduced through a plurality of input ports as the hydrocarbon feedstock flows through the first reactor section; further reacting the first output stream with aqueous nitric acid in a second reactor section to provide a second output stream; and recovering the at least one nitroalkane from the second output stream.

In yet another aspect, an apparatus for nitrating hydrocarbons is provided. The apparatus comprises: a reactor having an inlet for receiving a hydrocarbon feedstock and an outlet for releasing a reaction product; a packing material in the reactor; and a plurality of ports for introducing nitric acid at a plurality of distinct locations in the reactor, such that the hydrocarbon feedstock undergoes sequential reactions with nitric acid as the hydrocarbon feedstock flows from the inlet to the outlet.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a schematic diagram of the reactor for synthesizing at least one nitroalkane, in accordance with an illustrative embodiment.

DETAILED DESCRIPTION

In one aspect, a process for synthesizing at least one nitroalkane is provided. This process can operate in an isothermal or near-isothermal manner, beneficially resulting in high selectivity towards a desired nitroalkane, high reactor productivity (lb product/unit of reactor volume), and high raw material conversion. In another aspect, an apparatus for carrying out an isothermal or near-isothermal alkane nitration process is provided. The apparatus may include a reactor design that reduces potential corrosion issues.

FIG. 1 illustrates an apparatus 100 for synthesizing at least one nitroalkane. The apparatus 100 may include a reactor 101 that has at least a first reactor section 102 and a second reactor section 103. A hydrocarbon feedstock 104 may be reacted with a plurality of aqueous nitric acid flows 105a-j at a reactor pressure and a reaction temperature in a first reactor section 102 to produce a first reaction product 106. The first reactor section 102 may have an inlet 107 for receiving the hydrocarbon feedstock 104 and an outlet 108 for releasing the first reaction product 106. The hydrocarbon feedstock 104 and the aqueous nitric acid in the aqueous nitric acid flows 105a-j may react at a reactor pressure and a reaction temperature, such that the first reaction product 106 includes at least one desired nitroalkane. The first reaction product 106 may include, for example, 2-nitropropane. The hydrocarbon feedstock 104 may be sequentially exposed to the aqueous nitric acid flows 105a-j as the hydrocarbon feedstock 104 flows through at least a portion of the first reactor section 102. For example, the hydrocarbon feedstock 104 may be exposed to between five and ten flows of aqueous nitric acid 105a-j. In an illustrative embodiment, the hydrocarbon feedstock 104 may be first exposed to aqueous nitric acid flow 105a, then to aqueous nitric acid flow 105b, then to aqueous nitric acid flow 105c, then to aqueous nitric acid flow 105d, then to aqueous nitric acid flow 105e, then to aqueous nitric acid flow 105f, then to aqueous nitric acid flow 105g, then to aqueous nitric acid flow 105h, then to aqueous nitric acid flow 105i, and then to aqueous nitric acid flow 105j.

In one example, the hydrocarbon feedstock 104 may consist essentially of propane and acetic acid. In other examples, the hydrocarbon feedstock 104 may include, without limitation, one or more of the following: alkanes and cycloalkanes (including alkyl substituted cycloalkanes), such as propane, isobutane, n-butane, isopentane, n-pentane, n-hexane, n-heptane, n-octane, 2,3-dimethylbutane, cyclohexane, cyclopentane, and methylcyclohexane; aryl alkanes such as ethylbenzene, toluene, xylenes, isopropyl benzene; 1-methylnaphthalene and 2-methylnaphthalene and 4-methylbiphenyl; fused cycloalkanes, alkyl substituted fused aryl compounds, fused cyclolkane-aryl compounds (including alkyl substituted derivatives), such as tetralin, decalin, and methylnaphthalene; and carboxylic acids, such as acetic acid, propanoic acid, butanoic acid, and hexanoic acid. The nitration of reactants that already have one or more nitro substituents is also contemplated provided that the reactant still has an available hydrogen.

The first reactor section 102 and the second reactor section 103 may also be packed with a packing material 109 and a packing material 110, respectively, to improve reactant mixing and heat transfer and/or to vary the reactor volume. Packing of the reactor may be preferred, for example, in a propane nitration system where it is desired to increase the concentration of 2,2-dinitropropane in the product stream. Suitable packing materials 109 and 110 include, for example, random packing (for example, 1½" Pall Rings, IMTP®, or Cascade Mini-Rings®), or structured packing, such as those typically employed in distillation devices. Other packing materials are known in the art and may be used.

The first reactor section 102 may comprise a corrosion-resistant material, such as titanium, zirconium, or tantalum. For example, the corrosion-resistant material could be in a liner, which may be exposed to the hydrocarbon feedstock 104 and the aqueous nitric acid 105a-j as they react in the first reactor section 102.

Flowmeters 111a-j may be used to control the flow rate of aqueous nitric acid in each flow 105a-j. The aqueous nitric acid flows 105a-j also may be positioned to provide different times between successive exposures of the hydrocarbon feedstock 104 to the aqueous nitric acid flows 105a j. Further, the concentration of the aqueous nitric acid in each aqueous nitric acid flow 105a-j could be varied. The aqueous nitric acid flows 105a-j could also be heated prior to entering the first reactor section 102.

The hydrocarbon feedstock 104 may be sequentially reacted with aqueous nitric acid flows 105a-j in a first reactor section 102 to provide a first reaction product 106. The first reaction product 106 may comprise at least one nitroalkane, for example 2-nitropropane. The aqueous nitric acid flows 105a-j may be introduced through a plurality of input ports 112a-j as the hydrocarbon feedstock 104 flows through the first reactor section 102. The first reactor section 102 may essentially operate isothermally, such that the average temperature range in each reactor section between each input port 112a-j is less than 40 degrees Celsius, preferably less than 30 degrees Celsius, and more preferably less than 20 degrees Celsius. The aqueous nitric acid flows 105a-j may also be introduced with the hydrocarbon feedstock 104 through the inlet 107. The first reaction product 106 may further react with residual aqueous nitric acid in the second reactor section 103 to provide a second reaction product 113. The second reaction product 113 may contain more of a desired nitroalkane, for example 2-nitropropane, than the first reaction product 106.

The aqueous nitric acid flows 105a-j may be delivered to the first reactor section 102 in the form of an aqueous solution that contains at least about 10 weight percent, preferably at least about 15 weight percent, more preferably at least about 20 weight percent, of the acid. Further, the solution may contain less than about 50 weight percent, preferably less than about 40 weight percent, more preferably less than about 35 weight percent, and further preferably less than about 30 weight percent, of the acid. In other embodiments, the nitric acid solution may contain between about 15 and about 40 weight percent of the acid. In further embodiments, the nitric acid solution may contain between about 18 and about 35 weight of the acid.

The mole ratio of the hydrocarbon feedstock 104 to the aqueous nitric acid in the aqueous nitric acid flows 105a-j may be at least about 0.3:1, more preferably at least about 0.5:1.

The reactor pressure may be at least about 500 psi (34 atm), preferably at least about 1000 psi (68 atm), more preferably at least about 1200 psi (82 atm), and further preferably at least about 1300 psi (87 atm). In some embodiments, the pressure may be about 1600 psi (109 atm) or less, preferably about 1500 psi (102 atm) or less, more preferably about 1400 psi (95 atm) or less. In other embodiments, the pressure may between about 1000 psi (68 atm) and 1400 psi (95 atm). Various methods known in the art may be used for maintaining the pressure within the desired range including, for example, through the use of a back-pressure regulator.

The reaction temperature within the first reactor section 102 may be controlled (for example, by balancing the heat of reaction with the flowrate, concentration, and temperature of the nitric acid injections) to at least about 140 degrees Celsius and to less than about 325 degrees Celsius. In other embodiments, the temperature may be at least about 215 degrees Celsius and to less than about 325 degrees Celsius. In some embodiments, the temperature may be at least about 180 degrees, at least about 200 degrees, at least about 230 degrees, or at least about 240 degrees. In other embodiments, the temperature may be less than about 290 degrees, less than about 280 degrees, less than about 270 degrees, or less than about 250 degrees. In further embodiments, the temperature may be between about 200 and 250 degrees Celsius. In yet further embodiments, the temperature may be between about 215 and 280 degrees Celsius, or between about 220 and 270 degrees Celsius.

The overall residence time of the reactants in the reactor 101 may be preferably at least about 30 seconds, more preferably at least about 90 seconds. Residence time may be controlled in various ways including, for example, by the length and/or width of the reactor or through the use of packing material. Residence time may be determined by dividing the volume of the reactor by the inlet flow rates.

The reactor 101 may be a downflow configured reactor. That is, the reactor, which is preferably of an elongated and linear shape, such as a tube shape, may be positioned so that reactants are added through an entry port at or near the top of the reactor and then flow down the reactor for a residence time that is sufficient to allow reaction to occur and formation of the desired product. The product mixture may be collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing. Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increase liquid residence time and therefore oxidation chemistry as compared to a downflow reactor. A further disadvantage of coiled reactors is that they are not well-suited for industrial scale production because of the difficulty of fabricating large scale reactors in this shape.

A liquid loading rate in the reactor 101 may be between about 0.05 to 60 gpm/ft$^2$ (gallons of liquid flow per square foot of empty tower cross-sectional area), preferably between about 2 and 40 gpm/ft$^2$, and more preferably between about 25 and 35 gpm/ft$^2$.

A packing void fraction in the reactor 101 may be greater than 65 percent, preferably greater than 90 percent, and more preferably greater than 95 percent. The dry packing specific surface area may be between about 10 ft$^2$/ft$^3$ and 700 ft$^2$/ft$^3$.

Ladder distributors or other gas-liquid contractors such as spray towers may be used to properly distribute the aqueous nitric acid into the reactor 101.

The second reactor section 103 may comprise a corrosion-resistant material, such as titanium, zirconium, or tantalum. For example, the corrosion-resistant material could be in a liner which may be exposed to the first reaction product 106 and residual aqueous nitric acid as they react.

EXAMPLES

Various examples of the invention are demonstrated using a computer simulation of adiabatic mixers and reactors (for Examples 1-2) and a lab scale reactor (for Examples 3-6).

The lab scale reactor is a single tube shell-and-tube heat exchanger with a thermowell located axially down the center of the reactor in order to determine the temperature profile along the reactor's length. The reactor is 36" long (for Examples 3-5) and 30" long (for Example 6) and has a shell which is 1.25" OD 304 stainless steel with a ½" OD (0.37" ID) type 2 titanium process tubing and a ⅛" OD (0.093" ID) type 2 titanium thermowell. A very fine, movable thermocouple is inserted into the thermowell for the temperature profile measurement. The thermowell can be removed and the reactor filled with packing. The reactor is mounted vertically. The nitric acid and propane reactant streams are mixed in a Swagelok® "T" fitting at room temperature prior to entering the reactor. Hot oil is fed to the reactor shell countercurrent to the reactants. The reactor effluent (reaction product) is cooled in a shell-and-tube heat exchanger using water as the coolant. The effluent is then depressurized with the gases and liquids collected, measured, and analyzed.

In Examples 3-6 below, the mass balance of the nitration reaction is determined by GC/MS for gases, aqueous, nitroparaffin oil, and scrubber liquids, Karl Fisher titration for water content, potentiometric titration for strong/weak acid quantification, and HPLC for weak acid identification and quantification.

Metrics shown in the Tables below are calculated as follows:

Nitric Acid conversion(%)=100×(Nitric Acid in−Nitric Acid out)/Nitric Acid in;

Propane conversion(%)=100×(Propane in−Propane out)/Propane in;

Nitric Acid yield=g nitric acid consumed/g nitroparaffins formed;

Organic yield=g propane and acetic acid consumed/g nitroparaffins formed;

Nitromethane selectivity(%)=100×g nitromethane/g nitroparaffins formed;

Nitroethane selectivity(%)=100×g nitroethane/g nitroparaffins formed;

1-nitropropane selectivity(%)=100×g 1-nitropropane/g nitroparaffins formed;

2-nitropropane selectivity(%)=100×g 2-nitropropane/g nitroparaffins formed.

Grams of nitric acid consumed is calculated by subtracting the moles of nitric oxide in the reaction product from the moles of nitric acid in the feed and then converting the number of moles to grams using the molecular weight of nitric acid.

Grams of nitroparaffins include: nitromethane, nitroethane, 1-nitropropane, and 2-nitropropane.

Example 1

Effect of Multiple Input Ports on Temperature Rise Using 30 Weight Percent Nitric Acid Propane and acetic acid are reacted with 30 weight percent aqueous nitric acid at a reaction temperature of 180 degrees Celsius, a reactor pressure of 1300 psi (87 atm), a residence time of about 120 seconds, and a propane to nitric acid mole ratio of about 1.4:1. The aqueous nitric acid feed is split evenly between ten input ports. Additional aqueous nitric acid is added at 30 degrees Celsius. The feed rates are shown in Table 1.

TABLE 1

Feed rates for reaction using reactor with multiple input ports

| Component | Feed Rate |
| --- | --- |
| Propane | 147 lb/hr |
| Acetic acid | 243 lb/hr |
| Nitric acid (total) | 150 lb/hr |
| Water (total) | 350 lb/hr |

Table 2 shows a comparison of temperatures for the above nitration reaction using a reactor with ten input ports with the same reaction using a reactor with only one input port.

TABLE 2

Comparison of temperatures for the reaction using reactor with multiple input ports to the temperatures using a reactor with one input port 10 Input Port Reactor Summary

| Reaction Stage | Temperature in, degrees C. | Temperature out, degrees C. | Average Temperature, degrees C. | Temperature range in reaction stage, degrees C. |
| --- | --- | --- | --- | --- |
| 1 | 180 | 208.3 | 194.15 | 28.3 |
| 2 | 182.8 | 207.5 | 195.15 | 24.7 |
| 3 | 187.8 | 208.1 | 197.7 | 20.8 |
| 4 | 190.0 | 209 | 199.95 | 18.1 |
| 5 | 193.9 | 209.8 | 201.85 | 15.9 |
| 6 | 196.4 | 120.6 | 203.5 | 14.2 |
| 7 | 198.4 | 211.4 | 204.9 | 13 |
| 8 | 200.2 | 212.1 | 206.15 | 11.9 |

TABLE 2-continued

Comparison of temperatures for the reaction using
reactor with multiple input ports to the temperatures
using a reactor with one input port

| | | | | |
|---|---|---|---|---|
| 9 | 201.7 | 212.7 | 207.2 | 11 |
| 10 | 203.1 | 213.3 | 208.2 | 10.2 |
| Average | 193.47 | 210.28 | 201.875 | 16.81 |

1 Input Port Reactor Summary

| Temperature in, degrees C. | Temperature out, degrees C. | Average Temperature, degrees C. | Temperature range in reaction stage, degrees C. |
|---|---|---|---|
| 180 | 259.1 | 219.55 | 79.1 |

These two cases demonstrate the effect of splitting the nitric acid feed into ten equal parts as opposed to a single feed point. The temperature of the ten input port reactor is nearly isothermal with an average temperature range of 16.8 degrees Celsius in each reaction stage as opposed to 79.1 degrees Celsius for the reaction stage when using single inlet port. Using a reactor with additional input ports (more than ten) and/or modifying the nitric acid concentration or feed temperature to each port could be used to further reduce the temperature range in each reaction stage.

Table 3 shows the various temperatures ranges when using one, three, five, and ten input ports with 30 weight percent nitric acid and the process conditions above.

TABLE 3

Temperature ranges for various numbers of input ports
when using 30 weight percent aqueous nitric acid

| Number of Nitric Acid Feed Points | Nitric Acid Strength, wt % | Initial Temperature, degrees C. | Final Temperature, degrees C. | Average Temperature, degrees C. | Temperature Range, degrees C. |
|---|---|---|---|---|---|
| 1 | 30 | 180 | 259 | 219.5 | 79 |
| 3 | 30 | 180 | 228 | 204 | 48 |
| 5 | 30 | 180 | 220 | 200 | 40 |
| 10 | 30 | 180 | 213 | 196.5 | 33 |

Example 2

Effect of Multiple Input Ports on Temperature Rise Using 64 Weight Percent Nitric Acid Propane and acetic acid are reacted with 64 weight percent aqueous nitric acid at a reaction temperature of 180 degrees Celsius, a reactor pressure of 1300 psi (87 atm), a residence time of about 120 seconds, and a propane to nitric acid mole ratio of about 1.4:1. The aqueous nitric acid feed is split evenly between ten input ports. Additional aqueous nitric acid is added at 30 degrees Celsius. The feed rates are shown in Table 4.

TABLE 4

Feed rates for reaction using reactor with multiple input ports

| Component | Feed Rate |
|---|---|
| Propane | 147 lb/hr |
| Acetic acid | 243 lb/hr |
| Nitric acid (total) | 150 lb/hr |
| Water (total) | 85 lb/hr |

This example shows the effect of using higher strength nitric acid. It is believed that it is beneficial to balance the heat of reaction with the heat of vaporization of reactants. As described below, Example 2 suggests that using 64 weight percent aqueous nitric acid does not satisfy this balance nearly as well as using 30 weight percent aqueous nitric acid as in Example 1.

Table 5 shows a comparison of temperatures for the above nitration reaction using a reactor with ten inlet ports with the same reaction using a reactor with only one input port.

TABLE 5

Comparison of temperatures for the reaction using
reactor with multiple input ports to the temperatures
using a reactor with one input port 10 Input Port Reactor Summary

| Reaction Stage | Temperature in, degrees C. | Temperature out, degrees C. | Average Temperature, degrees C. | Temperature range in reaction stage, degrees C. |
|---|---|---|---|---|
| 1 | 180 | 214.1 | 197.05 | 34.1 |
| 2 | 199.8 | 228.6 | 214.2 | 28.8 |
| 3 | 216.3 | 239.4 | 227.85 | 23.1 |
| 4 | 228.7 | 247.5 | 238.1 | 18.8 |
| 5 | 238.3 | 253.9 | 246.1 | 15.6 |
| 6 | 245.8 | 259 | 252.4 | 13.2 |
| 7 | 252 | 263.1 | 257.55 | 11.1 |
| 8 | 257 | 266.4 | 261.7 | 9.4 |

TABLE 5-continued

Comparison of temperatures for the reaction using
reactor with multiple input ports to the temperatures
using a reactor with one input port

| | | | | |
|---|---|---|---|---|
| 9 | 261.2 | 269.2 | 265.2 | 8 |
| 10 | 264.7 | 271.6 | 268.15 | 6.9 |
| Average | 234.38 | 251.28 | 242.83 | 16.9 |

1 Input Port Reactor Summary

| Temperature in, degrees C. | Temperature out, degrees C. | Average Temperature, degrees C. | Temperature range in reaction stage, degrees C. |
|---|---|---|---|
| 180 | 284.2 | 232.1 | 104.2 |

These two cases demonstrate the effect of splitting the nitric acid feed into ten equal parts as opposed to a single feed point when using more concentrated aqueous nitric acid than in Example 1. The temperature of the ten input port reactor is not nearly isothermal as it continues to climb throughout the length of reactor. The average temperature range in each reaction stage is about the same as in Example 1 (16.9 degrees Celsius versus 16.8 degrees Celsius, respectively). However, the temperature continues to rise down the length of the reactor because, due to the higher aqueous nitric acid concentration, the net amount of heat provided by the reaction is greater than the amount of cooling. Thus, the reactor exit temperature is lower for the ten input port case than for the single input port case (271.6 degrees Celsius versus 284.2 degrees Celsius, respectively), but not by a large amount.

Table 6 shows the various temperatures ranges when using one, three, five, and ten input ports with 64 weight percent nitric acid and the process conditions above.

TABLE 6

Temperature ranges for various numbers of input ports when using 64 weight percent aqueous nitric acid

| Number of Nitric Acid Feed Points | Nitric Acid Strength, wt % | Initial Temperature, degrees C. | Final Temperature, degrees C. | Average Temperature, degrees C. | Temperature Range, degrees C. |
|---|---|---|---|---|---|
| 1 | 64 | 180 | 284 | 232 | 104 |
| 3 | 64 | 180 | 275 | 227.5 | 95 |
| 5 | 64 | 180 | 273 | 226.5 | 93 |
| 10 | 64 | 180 | 272 | 226 | 92 |

In Examples 3-6, only one input port is used, however, the small scale of the lab scale reactor, the high surface area to volume, and the reactor design allow for control of the temperature.

Example 3

Nitration of Propane at 180° C.

Propane and acetic acid are reacted in the above-described reactor with 30 weight percent aqueous nitric acid at reaction temperature of 180 degrees Celsius, a reactor pressure of 1400 psi (96.7 atm), and a residence time of 105 seconds (based on the volume of the reactor divided by the flow rate of the feeds at room temperature and 1400 psi). The propane to nitric acid mole ratio is about 1.9:1. The feed composition and the reaction product composition are summarized in Table 7 below.

TABLE 7

Feed composition and reaction product composition for the nitration of propane at 180° C.

| Component | Feed (g) | Reaction Product (g) |
|---|---|---|
| Propane | 562 | 436 |
| Nitric Acid | 424 | 1.5 |
| Water | 182 | 276 |
| Acetic Acid | 806 | 888 |
| Acetone | 0 | 14.0 |
| Nitromethane | 0 | 16.9 |
| Nitroethane | 0 | 1.1 |
| 2-Nitropropane | 0 | 173 |
| 1-Nitropropane | 0 | 20.9 |
| 2,2-Dinitropropane | 0 | 2.7 |
| Nitric Oxide | 0 | 40.0 |
| Nitrous Oxide | 0 | 7.6 |
| Nitrogen | 0 | 15.0 |
| Carbon Monoxide | 0 | 9.7 |
| Carbon Dioxide | 0 | 36.5 |

Key performance metrics for this reaction are summarized in Table 8.

TABLE 8

Key performance metrics for a reaction temperature of 180° C.

| Nitric Acid Conversion (%) | 99.6 |
|---|---|
| Propane Conversion (%) | 22.4 |
| Nitric Acid Yield | 1.60 |
| Organic Yield | 0.21 |
| Nitromethane Selectivity (%) | 8.0 |
| Nitroethane Selectivity (%) | 0.5 |

TABLE 8-continued

Key performance metrics for a reaction temperature of 180° C.

| 1-Nitropropane Selectivity (%) | 9.9 |
|---|---|
| 2-Nitropropane Selectivity (%) | 81.6 |

Example 4

Nitration of Propane at 200° C.

Propane and acetic acid are reacted in the above-described reactor with 30 weight percent aqueous nitric acid at a reaction temperature of 200 degrees Celsius, a reactor pressure of 1400 psi (96.7 atm), and a residence time of 120 seconds (based on the volume of the reactor divided by the flow rate of the feeds at room temperature and 1400 psi). The propane to nitric acid mole ratio is about 1.35:1. The feed composition and the reaction product composition are summarized in Table 9 below.

TABLE 9

Feed composition and reaction product composition for the nitration of propane at 200° C.

| Component | Feed (g) | Reaction Product (g) |
|---|---|---|
| Propane | 399 | 302 |
| Nitric Acid | 424 | 1.6 |
| Water | 182 | 300 |
| Acetic Acid | 807 | 838 |
| Acetone | 0 | 18.2 |
| Nitromethane | 0 | 26.6 |
| Nitroethane | 0 | 1.4 |
| 2-Nitropropane | 0 | 183 |
| 1-Nitropropane | 0 | 22.5 |
| 2,2-Dinitropropane | 0 | 1.9 |
| Nitric Oxide | 0 | 27.9 |
| Nitrous Oxide | 0 | 2.8 |
| Nitrogen | 0 | 5.2 |
| Carbon Monoxide | 0 | 5.9 |
| Carbon Dioxide | 0 | 27.0 |

Key performance metrics for this reaction are summarized in Table 10.

TABLE 10

| Key performance metrics for a reaction temperature of 200° C. | |
| --- | --- |
| Nitric Acid Conversion (%) | 96.9 |
| Propane Conversion (%) | 24.3 |
| Nitric Acid Yield | 1.57 |
| Organic Yield | 0.28 |
| Nitromethane Selectivity (%) | 11.4 |
| Nitroethane Selectivity (%) | 0.6 |
| 1-Nitropropane Selectivity (%) | 9.7 |
| 2-Nitropropane Selectivity (%) | 78.3 |

Example 5

Nitration of Propane at 235° C.

Propane and acetic acid are reacted in the above-described reactor with 30 weight percent aqueous nitric acid at a reaction temperature of 235 degrees Celsius, a reactor pressure of 1400 psi (96.7 atm), and a residence time of 120 seconds (based on the volume of the reactor divided by the flow rate of the feeds at room temperature and 1400 psi). The propane to nitric acid mole ratio is about 1.35:1. The feed composition and the reaction product composition are summarized in Table 11 below.

TABLE 11

| Feed composition and reaction product composition for the nitration of propane at 235° C. | | |
| --- | --- | --- |
| Component | Feed (g) | Reaction Product (g) |
| Propane | 599 | 428 |
| Nitric Acid | 635 | 2.4 |
| Water | 273 | 428 |
| Acetic Acid | 1210 | 1145 |
| Acetone | 0 | 41.1 |
| Nitromethane | 0 | 89.5 |
| Nitroethane | 0 | 4.0 |
| 2-Nitropropane | 0 | 288 |
| 1-Nitropropane | 0 | 42.1 |
| 2,2-Dinitropropane | 0 | 4.0 |
| Nitric Oxide | 0 | 33.9 |
| Nitrous Oxide | 0 | 1.8 |
| Nitrogen | 0 | 6.5 |
| Carbon Monoxide | 0 | 7.5 |
| Carbon Dioxide | 0 | 44.8 |

Key performance metrics for this reaction are summarized in Table 12.

TABLE 12

| Key performance metrics for a reaction temperature of 235° C. | |
| --- | --- |
| Nitric Acid Conversion (%) | 99.6 |
| Propane Conversion (%) | 28.5 |
| Nitric Acid Yield | 1.33 |
| Organic Yield | 0.56 |
| Nitromethane Selectivity (%) | 21.1 |
| Nitroethane Selectivity (%) | 1.0 |
| 1-Nitropropane Selectivity (%) | 9.9 |
| 2-Nitropropane Selectivity (%) | 68.0 |

Table 13 summarizes the nitromethane selectivity for reaction temperatures of 180° C., 200° C., and 235° C. from Examples 3-5, and shows that the nitromethane selectivity can be controlled over a wide range by varying the temperatures. Examples 3-5, also suggest that 2-nitropropane selectivity decreases with increased reaction temperature.

TABLE 13

| Nitromethane selectivity for various reaction temperatures | |
| --- | --- |
| Reaction Temperature, degrees C. | Nitromethane Selectivity |
| 180 | 8.0 |
| 200 | 11.4 |
| 235 | 21.1 |

Example 6

Effect of Internal Reactor Temperature on Nitromethane Weight Percentage

Propane and acetic acid are reacted in the above-described reactor with various strengths of aqueous nitric acid at reaction temperatures between 230 and 240 degrees Celsius, a reactor pressure of 1400 psig (96.7 atm), residence times from 106 to 121 seconds, and propane to nitric acid mole ratios from 3:1 to 4:1. The weight percentage of nitromethane produced is summarized in Table 14.

TABLE 14

| Weight percentage of nitromethane for various nitric acid strengths | | | | | |
| --- | --- | --- | --- | --- | --- |
| Run | Nitric Acid Strength (wt %) | Hot Oil Temperature, degrees C. | Peak Internal Reactor Temperature, degrees C. | Difference Between Peak Internal Temperature and Hot Oil Temperature, degrees C. | Nitromethane (wt %) |
| A | 47 | 230 | 333 | 103 | 5.6 |
| B | 40 | 240 | 287 | 47 | 2.2 |
| C | 35 | 235 | 272 | 37 | 0.6 |
| D | 20 | 240 | 242 | 2 | 0.8 |

As illustrated, higher nitric acid strength may result in a greater difference between the peak internal temperature and the hot oil (or reaction) temperature. The effect of the increased temperature difference is increased nitromethane formation, and thus decreased formation of other desired nitroalkanes, such as 2-nitropropane.

One goal of the isothermal or near-isothermal reaction design is to improve the selectivity for a desired nitroalkane. As illustrated in Examples 1 and 2, a near-isothermal reaction may be achieved with multiple input ports and a low aqueous nitric acid concentration. As illustrated in Examples 3-5, nitromethane selectivity may increase when the reaction temperature is increased. As illustrated in Example 6, nitromethane formation may increase (and 2-nitropropane formation may decrease) when aqueous nitric acid strength is increased. Thus, using a lower concentration of nitric acid and a plurality of input ports may result in increased selectivity and production of desired nitroalkanes, such as 2-nitropropane.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for synthesizing at least one nitroalkane, the process comprising:

reacting a hydrocarbon feedstock with aqueous nitric acid in a reactor at a reaction temperature of between about 140 degrees Celsius and about 325 degrees Celsius and at a reaction pressure of at least about $6.89 \times 10^6$ Pascal to produce a reaction product, wherein the hydrocarbon feedstock is sequentially exposed to a plurality of flows of aqueous nitric acid as the hydrocarbon feedstock flows through at least a portion of the reactor; and recovering the at least one nitroalkane from the reaction product.

2. A process according to claim 1, wherein the at least one nitroalkane is 2-nitropropane.

3. A process according to claim 1, wherein hydrocarbon feedstock is exposed to between five and ten flows of aqueous nitric acid.

4. A process according to claim 1, wherein the reactor comprises a titanium liner.

5. A process according to claim 1, wherein the reactor comprises a zirconium liner.

6. A process according to claim 1, wherein the reactor comprises a tantalum liner.

7. A process according to claim 1, wherein the reactor is downflow configured.

8. A process according to claim 1, wherein the reactor comprises random packing.

9. A process according to claim 1, wherein the reactor comprises structured packing.

10. A process according to claim 1, further comprising using flowmeters to control the flow rate of nitric acid in each flow.

11. A process according to claim 1, further comprising positioning the flows to provide different times between successive exposures of the hydrocarbon feedstock to the aqueous nitric acid.

12. A process according to claim 1, further comprising controlling the concentration of the aqueous nitric acid in each flow.

13. A process according to claim 1, further comprising heating the nitric acid prior to its entry into the reactor.

14. A process according to claim 1, wherein the concentration of aqueous nitric acid in each flow is between 10 and 40 weight percent.

15. A process for synthesizing at least one nitroalkane, the process comprising:

sequentially reacting a hydrocarbon feedstock with aqueous nitric acid in a first reactor section at a reaction temperature of between about 140 degrees Celsius and about 325 degrees Celsius and at a reaction pressure of at least about $6.89 \times 10^6$ Pascal to provide a first output stream, wherein the aqueous nitric acid is introduced through a plurality of input ports as the hydrocarbon feedstock flows through the first reactor section;

further reacting the first output stream with aqueous nitric acid in a second reactor section to provide a second output stream; and recovering the at least one nitroalkane from the second output stream.

* * * * *